United States Patent
Hurwitz et al.

(10) Patent No.: US 7,214,262 B2
(45) Date of Patent: May 8, 2007

(54) TEMPORARY COSMETIC DENTAL SURFACE COATING

(75) Inventors: Marni Markell Hurwitz, Far Hills, NJ (US); Dave Narasimhan, Flemington, NJ (US)

(73) Assignee: I Did It, Inc., Far Hills, NJ (US)

( * ) Notice: Subject to any disclaimer, the term of this patent is extended or adjusted under 35 U.S.C. 154(b) by 313 days.

(21) Appl. No.: 10/949,430

(22) Filed: Sep. 23, 2004

(65) Prior Publication Data
US 2006/0063853 A1    Mar. 23, 2006

(51) Int. Cl.
*A61C 5/00* (2006.01)

(52) U.S. Cl. .............. 106/35; 433/217.1; 523/115; 523/105; 427/2.1; 427/2.29; 424/401; 424/49; 424/52; 424/58; 424/600

(58) Field of Classification Search ............. 433/217.1; 106/35; 523/115, 105; 427/2.1, 2.29; 424/401, 424/49, 52, 58, 600
See application file for complete search history.

(56) References Cited

U.S. PATENT DOCUMENTS

| | | | | |
|---|---|---|---|---|
| 3,066,112 | A | * 11/1962 | Bowen ..................... 523/116 |
| 3,539,533 | A | * 11/1970 | Swartz et al. ............... 526/211 |
| 4,032,627 | A | 6/1977 | Suchan et al. ................ 424/54 |
| 4,097,994 | A | 7/1978 | Reaville et al. ............... 32/15 |
| 4,141,144 | A | 2/1979 | Lustgarten ..................... 32/15 |
| 4,310,584 | A | 1/1982 | Cooper et al. .............. 428/212 |
| 4,433,959 | A | 2/1984 | Faunce ....................... 433/201 |
| 4,473,353 | A | 9/1984 | Greggs ........................ 433/215 |
| 4,512,743 | A | 4/1985 | Santucci et al. ............ 433/217 |
| 4,682,950 | A | 7/1987 | Dragan ......................... 433/90 |
| 4,822,279 | A | 4/1989 | Greggs ..................... 433/202.1 |
| 4,992,049 | A | 2/1991 | Weissman .................... 433/215 |
| 5,407,973 | A | 4/1995 | Hasegawa et al. .......... 523/116 |
| 5,583,164 | A | 12/1996 | Jochum et al. .............. 523/115 |
| 5,968,998 | A | 10/1999 | Jochum et al. .............. 523/116 |
| 6,036,494 | A | 3/2000 | Cohen ..................... 433/217.1 |
| 6,210,163 | B1 | * 4/2001 | Cohen ..................... 433/217.1 |
| 6,652,280 | B2 | 11/2003 | Cohen ..................... 433/217.1 |
| 6,652,281 | B1 | 11/2003 | Eckhardt et al. ............ 433/219 |
| 6,709,271 | B2 | 3/2004 | Yin et al. ................. 433/228.1 |

OTHER PUBLICATIONS http://www.shellacepc.com/properties.html.

* cited by examiner

*Primary Examiner*—C. Melissa Koslow
(74) *Attorney, Agent, or Firm*—Ernest D. Buff & Associates, LLL; Ernest D. Buff; Theodore J. Pierson

(57) ABSTRACT

A temporary cosmetic dental coating has a transparent resin matrix containing embedded glass microspheres. The refractive index of the microspheres is at least 0.03 greater than the refractive index of the transparent resin matrix. Incoming light is reflected back in the same direction as it was emanated, providing a lustrous dental coating that is cosmetically appealing and covers dental defects and discoloration. The transparent resin matrix with glass microspheres is formed by mixing together a methacrylate based liquid monomer of methyl methacrylate or BIS-GMA and glass microspheres coated with activators/catalysts. The user applies the mixed composition to the teeth to form a temporary cosmetic dental coating, which is readily removed using a dental pick. A lac resin dissolved in ethyl alcohol is optionally mixed with glass microspheres and applied to teeth surfaces. The coating is hardened by alcohol evaporation and removed by alcohol dissolution.

6 Claims, 2 Drawing Sheets

TEMPORARY COSMETIC DENTAL SURFACE COATING

BACKGROUND OF THE INVENTION

1. Field of the Invention

The present invention relates to temporary coatings for teeth, that enhance their cosmetic appearance; and more particularly, to a coating comprising non-toxic components that is applied by the user.

2. Description of the Prior Art

Dentist applied procedures have long been available for improving the cosmetic appearance of teeth. Such procedures are recognized by the American Dental Association. They are typically applied at the dentist's office using commercially available preparations; and the cosmetic treatments are generally permanent. Such treatments include bleaching as discussed at http://www.ada.org/public/topics/whitening.asp using chairside bleaching procedures wherein the dentist applies a chemically oxidizing solution. The dentist may optionally use a special light or a laser light beam to activate the painted oxidizing agent. This chairside treatment takes typically 30 minutes, and several chairside procedures may be needed to achieve adequate teeth whitening. In an alternate bleaching procedure, the dentist prepares a custom fitted mouth guard that holds a bleaching gel suited for nighttime bleaching. This nighttime bleaching procedure may require repeated applications over several nights to achieve adequate teeth whitening.

Bonding techniques are commonly employed by the dentist wherein a matching tooth colored commercial preparation is applied to an etched enamel surface of the tooth to bond and cover discoloration, repair chips, breaks or cracks and fill in gaps as discussed at http://www.ada.org/public/topics/veneers.asp. With these bonding techniques a composite resin is shaped and hardened, using special ultraviolet light or chemical processes. The tooth with the hardened composite resin is smoothened and polished to appear natural. When properly applied such a bonding typically has a life expectancy of three to five years. Representative patents that disclose bonding procedures are discussed below.

Veneer is another technique used by dentists. It involves the use of a custom made shell that matches the color of the tooth, as discussed at http://www.ada.org/public/topics/veneers.asp. The veneer is fabricated by a dental technician or a commercial dental laboratory from a model provided by the dentist. Veneers are used to close gaps or cover teeth that are stained, poorly shaped or slightly crooked. Placing veneer is often an irreversible process, because small amounts of enamel are usually removed to accommodate the thickness of the veneer shell. The teeth underneath the veneer sometimes begin to decay, at which point a new replacement veneer is needed. Prior art teachings related to veneers wherein a glue or cement is used to attach a veneer and are discussed below.

U.S. Pat. No. 4,433,959 to Faunce discloses composite laminate dental veneer containing color systems. A composite laminate dental veneer is provided for attachment to the labial enamel surface of a human tooth. The dental veneer comprises an outer lamination composed of stain-resistant, chemical-resistant and erosion-resistant material, and an inner lamination composed of a material having the capability of efficient bonding to the labial enamel surface of the tooth. The inner lamination is adapted for permanent attachment to the outer lamination in such manner as to define an integral veneer mass. The laminate veneer also employs a color system embodying an additive color system which includes color pigments of an enamel blend and a subtractive color system which includes color pigments of a dentin color blend. These color pigments are distributed in color centers or microdots of color that are layered within a matrix. The veneer is glued to a prepared tooth surface. It does not form a coating applied by the user to unetched teeth.

U.S. Pat. Nos. 4,473,353, 4,822,279 to Greggs disclose a method for cosmetic restoration of anterior teeth, wherein a glazed porcelain veneer is bonded to a patient's tooth. A method and article for the cosmetic restoration of anterior teeth is provided whereby a glazed porcelain labial veneer is custom-made for a patient's tooth and thereafter chemically and mechanically bonded to such tooth, so as to provide a healthful and long-lasting cosmetic restoration of desired color, shape and esthetic appearance. This veneer is glued to a prepared tooth surface; it does not form a coating applied by user to unetched teeth.

U.S. Pat. No. 4,682,950 to Dragan discloses a device and method of bonding and veneering dental material to a tooth. An applicating device is used to cosmetically bond and veneer the teeth with composite dental material. A disposable syringe tip defines a reservoir that contains a predetermined amount of composite dental material. Connected to the syringe tip is a discharge end portion which narrows to a rectangularly shaped discharge orifice having a width of approximately 0.5 mm and a length of approximately 4 to 6 mm. The '950 patent discloses a permanent veneer of a thick strip, which is applied over surfaces of the teeth. No disclosure is contained therein concerning a temporary cosmetic coating for the teeth.

U.S. Pat. No. 4,992,049 to Weissman discloses a method for applying a veneer facing to a tooth. A veneer is secured onto a tooth substrate by a method comprising the steps of: 1) removing enamel in a matrix pattern, to a predetermined depth, from the lingual or buccal surfaces of the tooth; 2) removing the remaining outer enamel layer intermediate the matrix pattern, to the predetermined minimum depth, to provide a first, substantially level excavated enamel surface; 3) further excavating a plurality of compact areas on the first excavated enamel surface to an additional predetermined depth therebelow, but without exposing dentin, to form an indexed enamel surface; 4) taking an impression of such indexed enamel surface; and 5) obtaining from the mold a dental veneer, which can mate with such indexed excavated enamel surface and adhering the indexed veneer surface to the indexed enamel surface so as to accurately place the veneer on a tooth as an attractive outer labial or buccal surface. Preferably, the indexing grooves are undercut to improve adhesion. This veneer requires substantial preparation of tooth surface including excavation. The veneer application is permanent. It does not form a temporary cosmetic coating, which can be applied by the user.

Polymeric compositions have been proposed for use in dental applications. Representative patents disclosing such polymeric compositions are discussed below.

U.S. Pat. No. 3,066,112 to Bowen discloses dental filling material comprising vinyl silane treated fused silica and a binder consisting of BIS phenol and glycidyl acrylate. The composition has 70% of fused silica and 30% of polymer. Also disclosed are binder systems composed of the monomers, referred to in the art as BIS-GMA, admixed with other active monomers.

U.S. Pat. No. 4,097,994 to Reaville et al discloses a dental restorative composition containing glycidyl methacrylate derivative of bisphenol-A, sometimes referred to as bisphenol-A-bis-(3-methacrylato-2-hydroxypropyl) ether or, more conveniently, as oligomeric BIS-GMA resin and a ultraviolet photosensitizer, 4,4'-bis (dimethylamino) benzophenone, which also is known as Michler's ketone. Also disclosed is a dental restorative composition and tooth coating comprising the combination of an adhesive resin of the oligomeric BIS-GMA type, a low molecular weight reactive extender or diluent acrylate, an organic peroxide catalyst or free radical initiator and, as a photosensitizer, Michler's ketone. A rapidly photopolymerizable composition of the oligomeric BIS-GMA type suitable for dental restorative and tooth coating purposes is provided. Cure to a tack-free surface is obtained by the use of a particular ultraviolet sensitizer together with a peroxide catalyst. Exposure of the composition to actinic radiation produces singlet oxygen, which enters into the cross-linking reaction. However, because polymerization also takes place in the absence of oxygen, it is believed that an additional mechanism is operative. This BIS-GMA adhesive with ultraviolet sensitizer and peroxide catalyst requires UV radiation to effectively cure and harden the resin.

U.S. Pat. No. 5,407,973 to Hasegawa, et al. discloses a dental cold-polymerizing resin composition. In a powder-liquid type of dental cold-polymerizing resin composition, the powder component comprises a specific polymer such as polymethylmethacrylate containing a pyrimidinetrione derivative and an organometallic compound mixed at a specific proportion. The liquid component comprises a radical polymerizable compound containing an organic halogen compound and an aromatic tertiary amine mixed at a specific proportion used with a polymerization inhibitor.

U.S. Pat. Nos. 5,583,164 and 5,968,998 to Jochum, et al discloses dental compositions comprising bifunctional or polyfunctional acrylic-acid esters or methacrylic-acid esters. The dental compositions are based on an at least bifunctional or polyfunctional acrylic-acid and/or methacrylic-acid esters, which contain an initiator system for radical polymerization and which additionally contain a compound (1) of the general formula

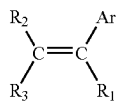

in which: Ar represents aryl or substituted aryl, $R_1$, $R_2$ and $R_3$ represent hydrogen, aryl or substituted aryl, straight-chain or branched chain $C_{1-18}$-alkyl, $C_{1-18}$-alkoxyl or $C_{1-17}$-alkoxycarbonyl, in which alkyl and alkoxyl can be substituted by halogen or aryl, in which, $R_1$ or $R_2$, when represented by aryl or substituted aryl, $C_{1-18}$-alkyl or $C_{1-18}$-alkoxyl, can be linked with Ar by a single-bond and in which, Ar, when represented by phenyl, $C_{1-18}$-alkylphenyl, $C_{1-18}$-alkoxylphenyl, carboxyl-$C_{1-17}$-alkylphenyl or halogenphenyl, $R_2$ can be represented by —O—, which is linked with the phenyl or phenyl moiety of Ar to a benzofuran, and in which at least one of $R_1$ to $R_3$ represents H, and at least one of $R_1$ to $R_3$ represents aryl or aryl substituted by a straight-chain or branched-chain $C_{1-18}$-alkyl, $C_{1-18}$-alkoxyl, carboxyl-$C_{1-17}$-alkyl or halogen. As a result of the content of a compound (I) the setting phase of the dental compositions is lengthened.

U.S. Pat. No. 4,310,584 to Cooper, et al. discloses multilayer light-reflecting film having a high refractive index thermoplastic polyester as the component of a system in which two or more resinous materials form a plurality of layers. A transparent thermoplastic resinous laminate film has at least 10 very thin layers of substantially uniform thickness. The layers are generally parallel, the contiguous adjacent layers are of different transparent thermoplastic resinous materials one of which is a thermoplastic polyester or copolyester resin having a refractive index of 1.55–1.61, and the adjacent resinous material has a refractive index which is lower by at least about 0.03. The contiguous adjacent layers differ in refractive index by at least about 0.03.

Representative patents disclosing application of a whitening coating to the surfaces of teeth are discussed below.

U.S. Pat. No. 4,032,627 to Suchan, et al. discloses a tooth whitening cosmetic composition. The tooth whitening covering cosmetic composition comprises Zinc Oxide, Water, Concentrated Ammonium Hydroxide and Ammonium Carbonate. It is used to form a complex system to cross-link the acrylic film forming resin Carboset Resin 514-A (B. F. Goodrich Chemical Co., of Cleveland, Ohio), which is used as a film former. After cross-linking and hardening of the resin, the free excess ammonium hydroxide is removed. Methyl cellulose (Methocel HG) is also disclosed for use as a film forming and pigment suspending agent. Ethanol is used as a solvent. The compound is said to have an extended wearing time. In practice, however, the composition is readily worn off by the abrasive action of food eaten after the compound is applied to the teeth, due to inherent softness of zinc oxide and cross-linked Carboset resin. The softness of the resin is also affected by the inability of the user to remove all the excess ammonium hydroxide following the cross-linking reaction of the Carboset Resin 514-A.

U.S. Pat. No. 4,141,144 to Lustgarten discloses a dental material and method for controlling tooth lustre. The dental material comprises a polymerizable binder, a polymerization agent and an additive comprising finely divided flakes of muscovite mica in a range of from about 1 to 20 percent by weight of the dental material for direct dental filling and restoration applications and in a range of from about 1 to 30 percent for cosmetically treating the surface of a tooth as a veneer or paint-on. The polymerizable resinous binder is 2,2-bis[4-3-methacryloxy-2-hydroxypropoxy)-phenyl]propane (BIS-GMA) with a reactive diluent; an activator and a peroxide catalyst. The use of muscovite mica provides a cosmetic treatment that is not durable due to the inherently low hardness of muscovite mica.

U.S. Pat. No. 4,512,743 to Santuchi et al. discloses a method for masking discoloration of teeth. The tooth surface is first etched with phosphoric acid to allow bonding to the composition. The polymerizable masking composition comprises liquid polymerizable acrylic monomer, a polymerization initiator for the monomer, sub-micron silica, and pigments, and is employed as a dental veneer to mask tooth discoloration. The polymerizable composition is a peroxide-catalyzed liquid difunctional acrylic ester composition comprising BIS-GMA, triethylene glycol dimethacrylate (TEGDM), fumed silica, pigments, a peroxide catalyst, and an accelerator for the catalyst. The monomer BIS-GMA is the diglycidyl dimethacrylate derivative of bisphenol-A; more precisely: 2,2-bis[4-(3-methacryloxy-2-hydroxypropoxy)phenyl]propane. The procedure is carried out in a dentist office; is not amenable to implementation by the user, since surface etching of teeth is involved. The fumed silica is extremely fine and does not reflect incident light with sufficient lustre.

U.S. Pat. No. 6,036,494 to Cohen discloses a composition and method for improving, altering, and treating teeth. The tooth is etched to create a bond with the composition, which covers discolorations or stains on the tooth's surface. The composition contains BIS-GMA polymer, an activator or catalyst such as benzoyl peroxide, and silica or titanium dioxide pigments. The tooth can be coated without etching procedure using glass ionomeric compound, which comprises pulverized fluoroaluminosilicate glass powder, carboxylic acid polymer, polymerizable unsaturated organic compound, and a polymerization catalyst. This glass ionomeric compound is light cured as discussed in Silverman E, et al., "A New Light-Cured Glass Ionomer Cement That Bonds Brackets To Teeth Without Etching In The Presence Of Saliva". Am. Jorthod Dentofac Orthop 1995; 108:231–6. and Silverman E. et al., "Bonding Of Orthodontic Attachments Using Ultraviolet Light Polymerized Adhesives". Buonocore M G (Ed.), "The Use Of Adhesives In Dentistry", Charles C. Thomas, Publisher, Springfield, Ill., 1975: 372–88. Both procedures require assistance of a dentist to apply the dental coating, since etching is involved in the first procedure and ultraviolet curing is needed in the second procedure. The glass ionomeric compound in these procedures is crushed fine powder of fluoroaluminosilicate glass, which is opaque and does not reflect light.

U.S. Pat. No. 6,210,163 to Cohen discloses a composition and method for cosmetically improving and altering the appearance of teeth. The teeth are first etched by the user. Weak acids such as citric acid and/or polyacrylic acid prepare the teeth surface to receive the lac based coloring compound. The lac based covering composition comprises a pigment compound selected from titanium dioxide, pulverized fluroaluminosilicate glass particles colorized by food coloring dye covered with a lac composition. This lac-based covering composition is opaque and covers stains or discolorations of the teeth. No disclosure is contained by the '163 patent concerning a composition containing a transparent glass which reflects light, thereby providing a lustrous coating for the teeth, and which can be applied to the teeth without need for etching or the like.

U.S. Pat. No. 6,652,280, to Cohen discloses a composition and method for improving, altering, and treating teeth. The teeth are first etched by the user with weak acids such as citric acid and/or polyacrylic acid, thereby preparing the teeth surfaces to receive a lac based coloring compound containing sodium fluoride to protect teeth dentin. The lac based covering composition comprises a pigment compound selected from titanium dioxide, pulverized fluroaluminosilicate glass particles colorized by food coloring dye covered with a fluoride containing lac composition. This lac based covering composition is opaque and covers stains or discolorations of the teeth. The composition does not contain a transparent glass, which reflects light, providing a lustrous coating to the teeth; it is not applied to the teeth without any etching requirement.

U.S. Pat. No. 6,652,281 to Eckhardt, et al. discloses dental materials. The dental materials contain monomers and/or prepolymers that can be subjected to a polymer-forming reaction. The dental materials comprise at least one initiating system and optionally comprise fillers, colorants, flow modifiers, stabilizers, ion-releasing substances as well as compounds which increase X-ray capacity or other modifiers. The dental materials are characterized by the presence of an initiating system proportioned such that the dental materials are sufficiently capable of flowing for at least 10 seconds after exposure to oxygen, whereupon they subsequently harden into a solid material. Polymer hardening occurs by oxidation. The dental material does not form a temporary surface coating for the teeth.

U.S. Pat. No. 6,709,271 to Yin, et al. discloses a low shrinkage dental composite, dental composite compositions, restorative compositions, and methods for their use. The compositions can contain (a) from about 1 to about 35 weight percent of a monomer portion capable of undergoing polymerization; (b) from about 75 to about 95 weight percent of a filler portion, the filler portion containing at least a spherical filler portion having at least one spherical filler particle component; and (c) from about 0.01 to about 10 weight percent of a polymerization catalyst portion capable of assisting in the polymerization and hardening of the composite. The spherical filler portion is present in an amount sufficient to reduce shrinkage of the composite after polymerization to about 1.8 percent or less. Compositions according to the invention are useful in Class I, II, IV, V, Core build-ups, and other types of dental restorations where maximum strength and polishability are desired. The spherical particles do not provide reflectivity of the incident light, and the composition is a permanent buildup composition, effected by cross-linking. It does not produce a temporary coating on the teeth surfaces.

Internet documents "Make Me Smile, Tooth Colored Fillings", www.smiledentalcare.net/makemesmiletoothcoloredfillings.htm, and www.dochowell.com/2whitfil.htm, disclose that white fillings are made from a tooth colored plastic mixture filled with microscopic glass beads (silicon dioxide) called composite resin. Such Internet documents teach a teeth-filling composition; but do not disclose or suggest a temporary cosmetic teeth coating, especially suited for application by the user.

Notwithstanding the efforts of prior art workers to provide cosmetic improvements to the teeth, the methods and means heretofore developed require tooth etching procedures that must be performed in a dentist office and result in permanent bonding of applied materials. It would be particularly desirable if a temporary coating could be safely applied by the user, at home, in a matter of minutes, to enhance reflectivity and appearance of the teeth.

SUMMARY OF THE INVENTION

The present invention provides a user applied temporary cosmetic dental coating composition especially suited for application by the user in a few minutes without need for etching the surfaces of the teeth. Generally stated, the coating composition comprises a polymerizable or hardenable transparent based resin composition into which are incorporated a plurality of nearly spherical retro reflective glass microspheres, the refractive index of the resin composition being less than that of the glass microspheres. Preferably, the refractive index of the polymerizable or hardenable resin is less than that of the glass microspheres by at least 0.03, whereby any light that is incident on the dental coating is reflected back by total internal reflection within the retro reflective glass microspheres. The dental coating composition is readily applied to the teeth surfaces by the user in a matter of minutes. It comprises a mixture of the resin and glass microspheres that can be mixed by the user immediately prior to application. The resin composition is preferably diluted with ethyl alcohol to retard the curing or hardening reaction of the resin. This provides the user sufficient time to mix and apply the temporary cosmetic dental coating composition to the unetched teeth. Application of the hardenable or curable temporary cosmetic dental coating composition to an unetched tooth prevents permanent bond formation between the coating and the teeth's dentin surface. As a result, the cured and hardened coating can be removed by the user at any time after application. Specifically, following application, the coating can be readily pried away by a dental pick or dissolved by application of ethyl alcohol. In any case, following a few weeks of usage, gradual seepage of saliva between the cured and hardened coating and the teeth surface lifts out the temporary cosmetic dental coating without causing damage to the teeth's dentin surface.

Glasses are considered to be solutions, rather than chemical compounds. About 95% of all glasses are of the "soda-lime" type, containing silicon dioxide (silica), Na2O (soda), and CaO (lime). Crown glass is a typical soda-lime-silica composition, and has a refractive index of 1.52–1.62. Flint glasses have a higher density and refractive index but are unsuitable for dental application since they contain 45–65% lead oxide. Barium glasses contain barium oxide instead of lead oxide. These barium glasses have a refractive index in the range of 1.55 to 1.82, comparable to lead-containing flint glasses. Schott 8235 is a barium glass marked by Schott Corporation for dental application and has a refractive index of 1.55. The composition of this Schott 8235 barium glass is $SiO_2 50$, $BaO 30$, $SrO 8$, $B_2O_3 10$, $Al_2O_3 10$. This glass is available in a standard grade K1. It has a mean diameter of $30 \pm 10$ microns for 50% of the grains, and 100% of the glass microspheres have a diameter less than 150 microns. Other suppliers of glass microspheres for reflective coatings include Swarko Industriers, P.O. Box 89, 907 N. James Campbell Blvd, Columbia, Tenn. 38402. Industrial size 9 of the glass microspheres marketed by Swarko industries has 95–100% of spherical particles in the size range of 150 microns. Industrial size 11 of the glass microspheres has 95–100% of the spherical glass particles in the 125 micron range. These particles are most suitable for the temporary cosmetic dental coating application. Such glass microsphere compositions are non-toxic and based on silica and other non-toxic oxides, which are not dissolved by the human digestive system The resin binders used to anchor the glass microspheres to the dental surface must be non-toxic and should harden within a reasonable period of time, preferably within 5 minutes, to facilitate application of the cosmetic dental composition by the user. The resin composition should not dissolve in or be attacked by saliva, so that its integrity is maintained. In addition, the resin composition must have a refractive index that is at least 0.03 less than the refractive index of the glass microsphere composition.

The first embodiment of the invention uses methacrylate based resins for attaching glass microspheres to unetched teeth surfaces. Unfilled methyl methacrylate resin has been in use for dental practice since 1950. Problems inherent to the unfilled resins, based on methyl methacrylate, include profound shrinkage during hardening, insufficient stiffness, and an excessive coefficient of thermal expansion as compared to the tooth structure. These very properties make methyl methacrylate resin and a resin binder suitable for temporary cosmetic dental coating. Polymethylmethacrylate, PMMA, has been approved by FDA for bone implant and is extensively used in dental molding and crown compositions. In its elementary form, the methyl methacrylate monomer polymerizes by additive polymerization. Methacrylate based polymeric coatings are designed to cure within 1 to 3 minutes so that the dentist can apply fillings, crowns or bridges without undue discomfort to the patient. During cure, a carbon double bond is broken to join with an adjoining monomer molecule. This addition polymerization is catalyzed and assisted by several peroxides, including benzoyl peroxide and other additives, including catalysts. These additives are then mixed with glass microsphere powder. When the powder is added to the resin and mixed, the polymerization of methyl methacrylate to polymethyl methacrylate occurs, creating a bond. The hardening reaction occurs so rapidly that the user has insufficient time to mix and apply a smooth coating on the tooth surface. It is desirable to extend the curing or hardening time of the methacrylate based resins, so that the user is provided sufficient time.

It has surprisingly been found that 95% ethyl alcohol, also known as grain alcohol, mixes readily with the methyl methacrylate monomer. When glass microsphere powder containing benzoyl peroxide is added to ethyl alcohol-diluted methyl methacrylate monomer, the polymerization reaction occurs slowly as the ethyl alcohol evaporates. This provides sufficient time for the user to mix glass microspheres containing hardening additives with diluted methacrylate monomer and apply the temporary cosmetic dental composition to the teeth surfaces with a brush. Furthermore, when the methacrylate based resin is sufficiently thinned with ethyl alcohol, for example, 40–60 percent level, the glass microsphere particle mixes more uniformly in the diluted resin mixture. This allows the final coating to be a single array of glass microspheres attached to the teeth, thereby providing a lustrous coating. If the methacrylate based resin is mixed with 5–30% of ethyl alcohol, the temporary cosmetic dental coating is generally thicker. A higher viscosity results, causing thicker multilayered coating of the arrays of glass microspheres on the teeth surfaces. In either case, the glass microspheres protrude beyond the cured and hardened layer of the temporary cosmetic dental coating, thereby reflecting incident light. A lustrous dental coating is thereby created, which provides a more cosmetically appealing dental surface especially suited to hide teeth discoloration or teeth faults.

Polymethylmethacrylate has a refractive index of 1.49, which is clearly at least 0.03 less than that of crown glass (refractive index 1.52) and 0.09 less than that of barium glass (refractive index 1.55).

More generally, the polymer component of the composition can be any methyl(meth)acrylate polymer such as methyl(meth)acrylate homopolymers and copolymers of methyl(meth)acrylate with alpha, beta-ethylenically unsaturated compounds such as vinyl acetate, alkyl (e.g., $C_2$–$C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred. The reactive monomer component is preferably methyl acrylate or methyl methacrylate, although the $C_2$–$C_4$ alkyl(meth)acrylates, such as ethyl(meth)acrylate, propyl(meth)acrylate or (n-, or iso-)butyl(meth)acrylate, can also be used. These resin materials, which are themselves well known and commercially available, are usually provided with mixtures of the finely divided polymer and liquid monomer, and are characterized as being self-polymerizable when mixed, together with a polymerization catalyst, such as dibenzoyl peroxide, and polymerization accelerator, such as dimethyl-p-toluidine. The pasty mass will harden in situ, at room temperature (via an exothermic reaction) within a few minutes.

There is another group of methacrylates based on BIS-GMA (bisphenol A-glycidyl methacrylate) system (an aromatic or urethane diacrylate oligomer) that are also suitable for the temporary cosmetic dental coating. The "BIS-GMA" is the condensation product of two moles of methacrylic acid and the diglycidyl ether of bisphenol A or alternatively two moles of glycidyl methacrylate with one mole of bisphenol A and has the following chemical nomenclature; 2,2-bis[4-(3-methacryloxy-2-hydroxypropxy)-phenyl]-propane. A bisphenol A dimethacrylate can also be added to BIS-GMA, if desired. The polymerization of BIS-GMA requires suitable activators, for example, N,N-dimethyl-para-toluidine, para-tolemenesulfinic acid and N,N-dialkylanilines and benzoyl peroxide or persulfate catalyst. The activators and the catalyst are coated on the glass microsphere powder, which is added to the BIS-GMA resin to formulate the temporary cosmetic dental composition. The viscosity of BIS-GMA is reduced by the addition of a reaction diluent such as, for example, methyl methacrylate, ethylene or triethylene glycol dimethacrylate and tetraethylene glycol dimethacrylate. It has been found that 95% ethyl alcohol, also known as grain alcohol, may be used as a diluent to retard the polymerization reaction and provide sufficient time for the application of the temporary cosmetic dental composition to the teeth.

In a second embodiment, bleached shellac, also known as "lac", is used as the resin retaining glass microspheres in the temporary cosmetic dental coating. Lac is soluble in ethyl alcohol and quickly dries as ethyl alcohol evaporates, forming a hardenable resin matrix. Shellac is safe for human use. It is certified by FDA as a food additive, and shellac based coatings are not dissolved or affected by saliva. The lac coating can be easily removed by the application of ethyl alcohol. Shellac or bleached lac is disclosed at http://www.shellacepc.com/properties.html as having a refractive index of 1.52, and is therefore suitable for use with glass microspheres of barium glass powder to form the temporary cosmetic dental coating of the invention.

BRIEF DESCRIPTION OF THE DRAWING

The invention will be more fully understood and further advantages will become apparent when reference is had to the following detailed description of the preferred embodiments of the invention and the accompanying drawings, in which.

DETAILED DESCRIPTION OF THE INVENTION

Figure 1:
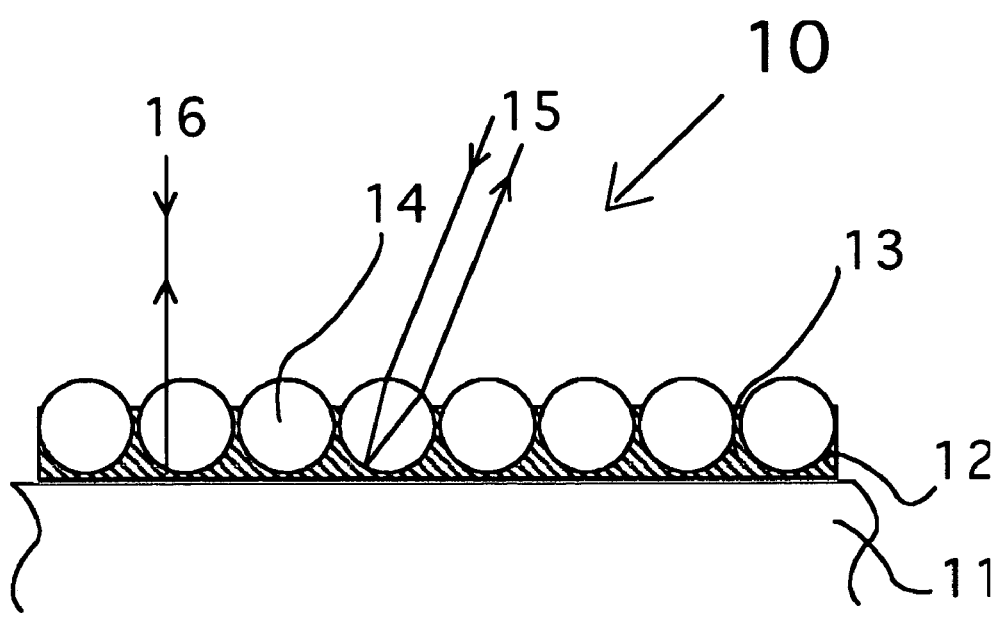
FIG. 1 is a schematic diagram of a temporary cosmetic dental coating having a single array of glass microspheres embedded in a lower refractive index resin, showing the reflection of incident light.

Improving the cosmetic appearance of the teeth by application of a dental composition requires that the composition have appropriate viscosity to be easily paintable with a brush. The composition should also harden in a short period of time, producing a temporary cosmetic dental coating that is unaffected by saliva and is also non-toxic. These requirements are met by compositions that contain glass microspheres and a resin composition of the polymerized methyl methacrylate type or lac resin.

The lustrous appearance of the cosmetic composition coated teeth is primarily due to the retro reflective character of the cosmetic dental coating. The glass microspheres incorporated within the cosmetic dental coating redirects any incoming light back to the source due to internal total reflection, which occurs when light enters a glass microsphere. This phenomenon is extensively used in street markings and highways signs. A key requirement involves incorporation of the glass microsphere within a resin having a lower refractive index than that of the glass microsphere. The refractive index of the resin must be 0.03 less than that of the glass microspheres or better, to provide this total internal reflection effect. However, the light which is incident normal to the surface penetrates the glass microsphere without being affected. Thus the underlying teeth surfaces are seen as white surfaces when a single array of glass microspheres is present. When multiple arrays of glass microspheres are stacked one above the other, any incoming light is effectively scattered and returned back, providing a white appearance. Advantageously, the effect created by this process completely covers and masks any defects in the teeth.

Glass microspheres are non toxic, since they contain silicon dioxide and other oxides forming nearly a complete solution. None of these oxides can be dissolved by human digestive system. The high hardness of the glass provides extreme wear resistance for the cosmetic dental coating when a variety of food materials are chewed.

The resin binder suitable for use with glass microspheres to form the composition of the present invention may include any conventional binder used in the field of dental work. The most frequently used binders include, for example, acrylic monomers or comonomers alone or in combination, such as methacrylate esters, i.e. methyl methacrylate, ethyl methacrylate and the higher methacrylate esters such as n-propyl, isopropyl, n-butyl, isobutyl or glycol di-methacrylate, polymethacrylates, and/or methyl, ethyl or isopropyl cyanoacrylates.

In its most simple form, polymerized methyl methacrylate is a common polymer used in dental profession from 1950. The polymethyl methacrylate is formed by additive polymerization as shown below wherein a carbon double bond is broken to polymerize the methyl methacrylate moleculae as shown below. This reaction is assisted by free radical initiators such as benzyol peroxide.

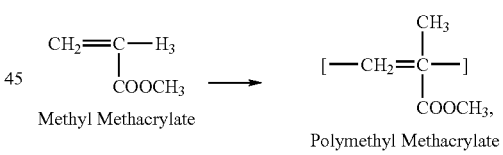

Methyl Methacrylate → Polymethyl Methacrylate

The methyl methacrylate liquid monomer polymerizes when benzoyl peroxide is added forming a solid hardened mass. The glass microspheres may be coated with benzoyl peroxide and when the liquid is mixed with the glass microspheres the hardening reaction begins. Since this reaction can be rapid, it is difficult to judge the time available for coating the teeth surface using a brush. If the resin hardens prematurely, rough coating is produced. It has been surprisingly found that addition of 95% ethyl alcohol to the methyl methacruylate monomer liquid slows down the curing or hardening time providing ht use more controlled application time. It is presumed that the evaporation of the ethyl alcohol occurs before the benzoyl peroxide can break down the double bond of the methyl methacrylate monomer. Since ethyl alcohol is non-toxic, the overall temporary cosmetic dental composition is non-toxic.

More generally, the polymer component of the composition can be any methyl(meth)acrylate polymer such as methyl(meth)acrylate homopolymers and copolymers of methyl(meth)acrylate with alpha, beta-ethylenically unsaturated compounds such as vinyl acetate, alkyl (e.g., $C_2$–$C_6$) (meth)acrylates and multi-functional acrylic monomers such as alkylene dimethacrylate and alkylene diacrylates and triacrylates. These polymers generally have a molecular weight between 500,000 and 2,000,000. Methylmethacrylate homopolymers and copolymers are preferred. The reactive monomer component is preferably methyl acrylate or methyl methacrylate although the $C_2$–$C_4$ alkyl(meth)acrylates, such as ethyl(meth)acrylate, propyl(meth)acrylate or (n-, or iso-)butyl(meth)acrylate, can also be used. These resin materials, which are themselves well known and commercially available, are usually provided with mixtures of the finely divided polymer and liquid monomer, and are characterized as being self-polymerizable when mixed, together with a polymerization catalyst, such as dibenzoyl peroxide, and polymerization accelerator, such as dimethyl-p-toluidine. The pasty mass will harden in situ, at room temperature (via an exothermic reaction) within a few minutes.

Epoxies harden by a ring opening mechanism at room temperature and adhere to teeth. But amine cured epoxies do not harden quickly enough for dental use. Development of quick-curing epoxies with acidic catalysts has not worked, since teeth surfaces function as a buffer producing poorly polymerized coatings. A monomer that resembles epoxies but has methacrylate groups, as discussed U.S. Pat. No. 3,066,112 to Bowen, provides an ideal methacrylate composition which hardens effectively. These methacrylates based on the BIS-GMA ("bisphenol A-glycidyl methacrylate") system or other aromatic or urethane diacrylate oligomer are also suitable for the temporary cosmetic dental coating. The polymer consists of a reaction product of bisphenol A and glycidyl methacrylate thinned with tetraethyleneglycol dimethacrylate and activated with dimethyl-para-toluidene. It hardens at room temperature in about 3 minutes, when mixed with glass microspheres containing benzoyl peroxide. Typically 5 parts of benzoyl peroxide is used for 100 parts of the resin.

The "BIS-GMA" is the condensation product of two moles of methacrylic acid and the diglycidyl ether of bisphenol A or alternatively two moles of glycidyl methacrylate with one mole of bisphenol A and has the following chemical nomenclature; 2,2-bis[4-(3-methacryloxy-2-hydroxypropxy)-phenyl]-propane. A bisphenol-A dimethacrylate can also be added to BIS-GMA if desired. The polymerization of BIS-GMA requires suitable activators, for example, N,N-dimethyl-para-toluidine, para-tolemenesulfinic acid and N,N-dialkylanilines and benzoyl peroxide or persulfate catalyst. The activators and the catalyst are coated on the glass microsphere powder, which is added to the BIS-GMA resin to formulate the temporary cosmetic dental composition. The viscosity of BIS-GMA is reduced by the addition of a reaction diluent such as, for example, methyl methacrylate, ethylene or triethylene glycol dimethacrylate and tetraethylene glycol dimethacrylate. It has been found that 95% ethyl alcohol, also known as grain alcohol, may be used as a diluent to retard the polymerization reaction and provide sufficient time for the application of the temporary cosmetic dental composition to the teeth.

The present method provides for the application of a BIS-GMA polymer mixed with glass microspheres to the surface of a tooth to cover discoloration which is present on the teeth surfaces. The covering compound is applied by a brush and hardens within a few minutes due to the polymerization reaction of the BIS-GMA. The BIS-GMA compound is manufactured by Bisco, Inc., of Itasca, Ill., under the name AELITESEAL.™. Pit and Fissure Sealant. This material is sold for filling posterior teeth and specifically for filling fissures in the teeth.

In a second embodiment, the temporary cosmetic dental coating composition includes a lac material, which is provided with a colorizing compound or substance to match with the desired shade of the teeth dissolved in a solvent such as ethyl alcohol. Lac is a natural resinous substance excreted by an insect, Laccifer Lacca, and has been used in dentistry. (See A. Azucca, R. Huggett, and A. Harrison, "The Production of Shellac and its General and Dental Uses: A review." Journal of Oral Rehabilitation, 1993, vol. 20, pp. 393–400; and I. Klineberg and R. Earnshaw, "Physical Properties of Shellac Baseplate Materials." Australian Dental Journal, October, 1967, vol. 12 no. 5, pp. 468–475.) Another use of shellac in dentistry includes treatment of a cavity with a hydrophilic shellac film placement of a polystyrene liner. (See M. Blixt and P. Coli, "The Influence of Lining Techniques on the Marginal Seals of Class II Composite Resin Restorations" Quintessence International, vol. 24, no. 3, 1993). Shellac has also been prepared and used in dentistry for the use of a bead adhesive for securing a composite resin veneer cast restoration. (See C. Lee, H. Pierpont, and E. Strickler, "The Effect of Bead Attachment Systems on Casting Patterns and Resultant Tensile Bond Strength of Composite Resin Veneer Cast Restorations", The Journal of Prosthetic Dentistry, November, 1991, vol. 66, no. 5, pp. 623–630.) Therefore shellac or lac compositions are non-toxic and may be used as a resin incorporating glass microspheres to produce a temporary cosmetic dental coating.

A refined bleached food grade dewaxed lac resin available commercially from Mantrose-Haeuser Company 1175 Post Road East, Westport, Conn. 06880, USA and is dissolved in ethyl alcohol. The glass microspheres with appropriate refractive index such as barium glass is added by the user to the ethyl alcohol formulation. This temporary cosmetic dental coating composition is applied by the user to the teeth surface using a paint brush. Ethyl alcohol evaporates, producing a cosmetic coating that has glass microspheres entrapped in a lac matrix. Depending on the dilution of the ethyl alcohol and the concentration of glass microspheres added, the coating may have a single layer or multiple layers of glass microspheres. The temporary cosmetic dental coating is durable due to the high hardness of glass beads and degradation resistance of lac compositions. The temporary cosmetic dental coating is readily removed by the user using ethyl alcohol, preferably applied by a brush, and wiping the cosmetic coating off. The lac in the cosmetic coating is dissolved by ethyl alcohol.

FIG. 1 is a schematic diagram 10 of the temporary cosmetic dental coating placed on a dental surface 11. The temporary cosmetic dental coating 12 comprises a resin matrix 13 with a single array of glass microsphers 14. The incident light along path 15 is reflected back as shown by the arrows due to internal reflection within the glass microsphere. This internal reflection occurs when the refractive index of the glass in the glass microsphere 14 is greater than that of the resin matrix 13 surrounding the glass microsphere. When a ray of light is incident normally as shown at 16, it illuminates the white teeth and is also internally reflected. As a result, the overall whiteness appearance of the teeth is enhanced providing a lustrous appearance.

Figure 2:
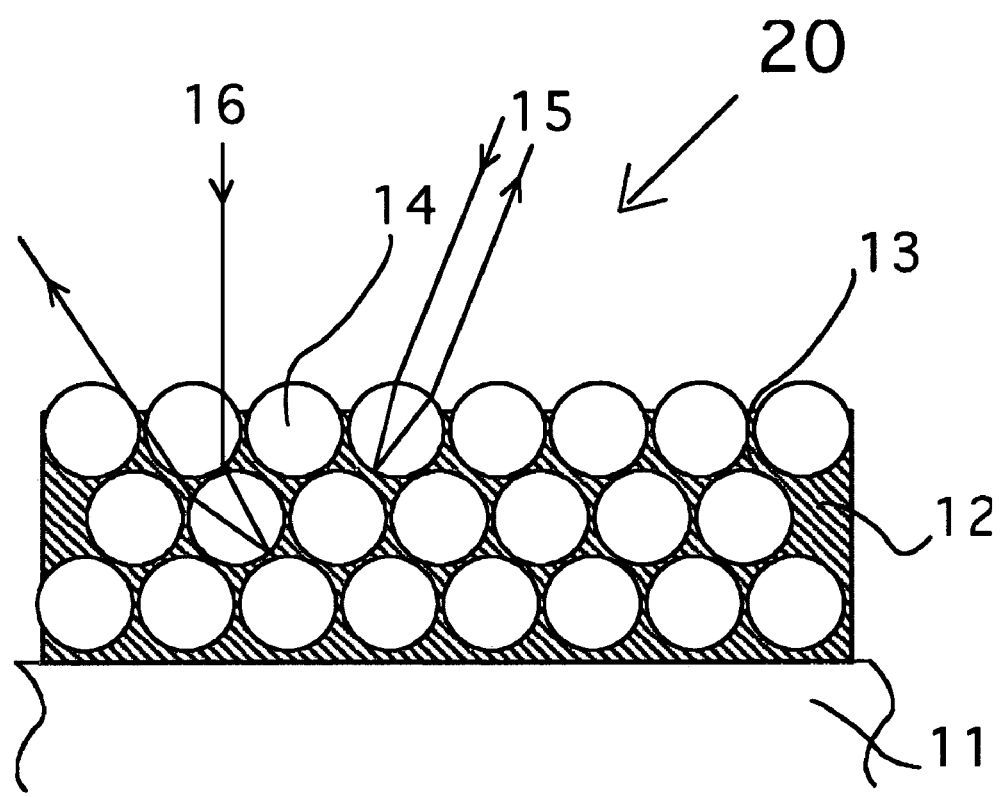
FIG. 2 is a schematic diagram of a temporary cosmetic dental coating having a multiple array of glass microspheres embedded in a lower refractive index resin, showing the reflection of incident light.

FIG. 2 is a schematic diagram 20 of the temporary cosmetic dental coating placed on a dental surface 11. The temporary cosmetic dental coating 12 comprises a resin matrix 13 with a multiple array of glass microspheres 14. The incident light along path 15 is reflected back as shown by the arrows due to internal reflection within the glass microsphere. This internal reflection occurs when the refractive index of the glass in the glass microsphere 14 is greater than that of the resin matrix 13 surrounding the glass microsphere. When a ray of light is incident normally as shown at 16, it illuminates the array of glass microspheres underneath and is scattered and eventually reflected back. As a result, any imperfections of the teeth are completely covered and the overall whiteness of the teeth is enhanced providing a lustrous appearance.

The key features of the temporary cosmetic dental surface coating includes, in combination, the features set forth below:

1. a cosmetic dental coating applied by the user without any etching of the teeth dentin surface;
2. the bond of the temporary cosmetic dental coating is weak and can be flaked off or dissolved at will without damaging the teeth dentin surface;
3. the temporary cosmetic dental coating comprises a liquid composition and glass microspheres which are mixed by the user to apply the cosmetic dental coating to the teeth and hardens to form a lustrous coating;
4. the glass microspheres reflect incident light back since the refractive index of the glass microsphere is greater than that of surrounding resin matrix by at least 0.03, thereby creating a lustrous cosmetic dental coating;
5. the glass microspheres have a diameter of 30 to 150 microns;
6. the resin matrix is formulated from methyl methacrylate monomer, which polymerizes, and the user mixes monomer liquid with glass microspheres coated with activators such as benzoyl peroxide;
7. the polymerization rate of methyl methacryalte and glass microsphere mix is reduced by dilution with ethyl alcohol;
8. the resin matrix is formulated from BIS-GMA monomer, which polymerizes, and the user mixes monomer liquid with glass microspheres coated with activators such as N,N-dimethyl-para-toluidine, para-tolemenesulfinic acid, N,N-dialkylanilines and benzoyl peroxide;
9. the polymerization rate of BIS-GMA and glass microsphere mix is reduced by dilution with ethyl alcohol;
10. the methacrylate temporary cosmetic dental coating is readily removed by flaking the coating off with a dental pick;
11. the resin matrix formulated from lac is dissolved in ethyl alcohol, and the user mixes glass microspheres to form temporary cosmetic dental surface coating composition which, when applied to the teeth surfaces, forms a coating that dries by the evaporation of ethyl alcohol;
12. the lac formulated coating is readily removed by an ethyl alcohol coating.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A process for applying a temporary cosmetic dental coating, comprising the steps of:
   a. selecting a liquid composition selected from a methyl metacrylate monomer or BIS-GMA methacrylic monomer;
   b. mixing the liquid composition with ethyl alcohol to control viscosity of said temporary cosmetic dental coating;
   c. adding glass microspheres coated with resin hardeners appropriate to the methacrylate resin;
   d. mixing the liquid composition comprising glass microspheres to initiate the resin hardening reaction;
   e. coating the surfaces of the teeth with the mixed liquid composition;
   f. smoothening the coating surface; and
   g. immobilizing the coated teeth surfaces for a few minutes to facilitate completion of the hardening reaction and production of the temporary cosmetic dental coating, said temporary cosmetic dental coating being readily applied to unetched teeth and removed by prying with a dental pick.

2. The process for applying a temporary cosmetic dental coating as recited by claim 1, wherein said glass microspheres have a diameter of 30 to 150 microns.

3. The process for applying a temporary cosmetic dental coating as recited by claim 1, wherein said glass microspheres are embedded as a single array reflecting incident light formed by a less viscous liquid composition diluted by 40 to 60% ethyl alcohol.

4. The process for applying a temporary cosmetic dental coating as recited by claim 1, wherein said glass microspheres are embedded as multiple arrays reflecting incident light formed by a viscous liquid composition diluted by 5 to 30% ethyl alcohol.

5. The process for applying a temporary cosmetic dental coating as recited by claim 1, wherein the surfaces of the teeth are coated with said mixed liquid composition with a brush.

6. The process for applying a temporary cosmetic dental coating as recited by claim 1, wherein said resin has a lower refractive index than that of said glass microspheres.

* * * * *